(12) United States Patent
Reeves

(10) Patent No.: US 6,213,953 B1
(45) Date of Patent: Apr. 10, 2001

(54) BLOOD PRESSURE CUFF

(75) Inventor: Johnnie R. Reeves, Phoenix, AZ (US)

(73) Assignee: American Medical Screening Ltd., Phoenix, AZ (US)

(*) Notice: Subject to any disclaimer, the term of this patent is extended or adjusted under 35 U.S.C. 154(b) by 0 days.

(21) Appl. No.: 09/473,257

(22) Filed: Dec. 27, 1999

(51) Int. Cl.[7] ....................................... A61B 5/02

(52) U.S. Cl. ................................ 600/499; 600/490

(58) Field of Search ................................ 600/499, 490, 600/491–497

(56) References Cited

U.S. PATENT DOCUMENTS

| | | | |
|---|---|---|---|
| 3,756,239 | * | 9/1973 | Smythe ................................ 600/499 |
| 3,906,937 | * | 9/1975 | Aronson ................................ 600/493 |
| 3,935,984 | * | 2/1976 | Lichowsky et al. ................ 600/499 |
| 5,025,793 | * | 6/1991 | Richley et al. ..................... 600/490 |
| 5,595,180 | * | 1/1997 | Ogura et al. ........................ 600/499 |

* cited by examiner

*Primary Examiner*—Cary O'Connor
*Assistant Examiner*—Navin Natnithithadha
(74) *Attorney, Agent, or Firm*—LaValle D. Ptak (57) ABSTRACT

An improved ausculatory blood pressure cuff, of the type used in self-testing locations, operates with no moving parts other than the inflatable bladder. No springs or mechanical motors are used to close the bladder portion of the machine around the arm of the user. A generally cylindrically shaped housing is mounted on a base support. The housing has an opening where it is mounted onto the base support; and a hollow fabric sleeve, having a first portion releasably attached to the interior of the cylindrical housing and having a second portion spaced from the first portion located on the interior of the housing, is placed in the housing. An inflatable bladder is located in the space between the two portions of the hollow sleeve; and air is supplied under pressure to inflate the bladder to predetermined pressures. When this is done, the bladder and sleeve expand to constrict the space in the cylindrical housing to close the bladder and sleeve about the arm of a user.

20 Claims, 6 Drawing Sheets

BLOOD PRESSURE CUFF

BACKGROUND

Blood pressure measuring devices are in widespread use to permit persons to undertake self-testing of blood pressure. Typically, these devices are installed in pharmacies, grocery stores, medical clinic lobbies and the like. The machines for taking and displaying the blood pressure data include a pressurization cuff, which is designed to encircle the upper arm of the person undergoing the test. In the past, the pressurization cuff was mounted in a generally cylindrically shaped housing on a spring which biased the cuff to its widest opening within the housing. After the person using the machine inserted his or her arm, the operating sequence for the blood pressure measurement was initiated. The sequence began with an electric motor winding a cloth band, attached to the spring, to tighten the spring carrying the blood pressure cuff around the arm of the person using the device. When the motor had tightened the cuff around the arm, the sequence for inflating a bladder in the cuff and sensing the blood pressure effected by pneumatic pressure in the bladder was accomplished.

The prior art device described above includes a number of components which, after repeated usage, result in the need for continuing maintenance and replacement of worn parts. The electric motor includes a solenoid and clutch for effecting its operation. These parts wear out. Provision must be made to sense the tightness of the cuff effected by the winding of the cloth band on a shaft by the motor. The cloth band, because it is wound and unwound in and out of the device frequently, exhibits wear over a period of time. The continuous flexing and releasing of the springs also creates a potential for mechanical failure.

In addition, the space which necessarily must be provided between one end of the cuff and the end which is moved by means of the winding and unwinding operation of the motor, creates a potential for pinching the flesh of obese or elderly persons in the gap where the flexible cloth band is pulled past the fixed end of the cuff.

It is desirable to provide an automatic blood pressure machine using a cuff which eliminates various mechanical parts of the prior devices, and which is not subject to pinching the arms of obese persons or elderly persons with loose skin.

SUMMARY OF THE INVENTION

It is an object of this invention to provide an improved blood pressure cuff apparatus.

It is another object of this invention to provide an improved blood pressure cuff apparatus which operates without mechanical tightening of the cuff prior to the application of pneumatic pressure.

It is an additional object of this invention to provide a blood pressure cuff for an automatic blood pressure machine which operates entirely on pneumatic pressure.

It is a further object of this invention to provide an improved blood pressure cuff for an automatic blood pressure machine which requires minimum maintenance.

In accordance with a preferred embodiment of the invention, an improved blood pressure cuff for an automatic blood pressure machine includes a base support. A generally cylindrically shaped housing is mounted on the base support; and this housing has an opening in its bottom cooperating with an opening in the base support, to which it is attached. The internal diameter of the cylindrical housing is larger than the external diameter of an arm to be inserted; and this cylindrical housing is open at both ends. A hollow sleeve is attached to the interior of the cylindrical housing and this sleeve has an inner portion and an outer portion, with an inflatable bladder located between the inner and outer portions of the sleeve. A provision is made for supplying air under pressure to the bladder to inflate it, and thereby constrict the sleeve or expand it into the space in the cylindrical housing. In addition, provision is made for removing air from the bladder when a test is completed.

DETAILED DESCRIPTION

Figure 1:
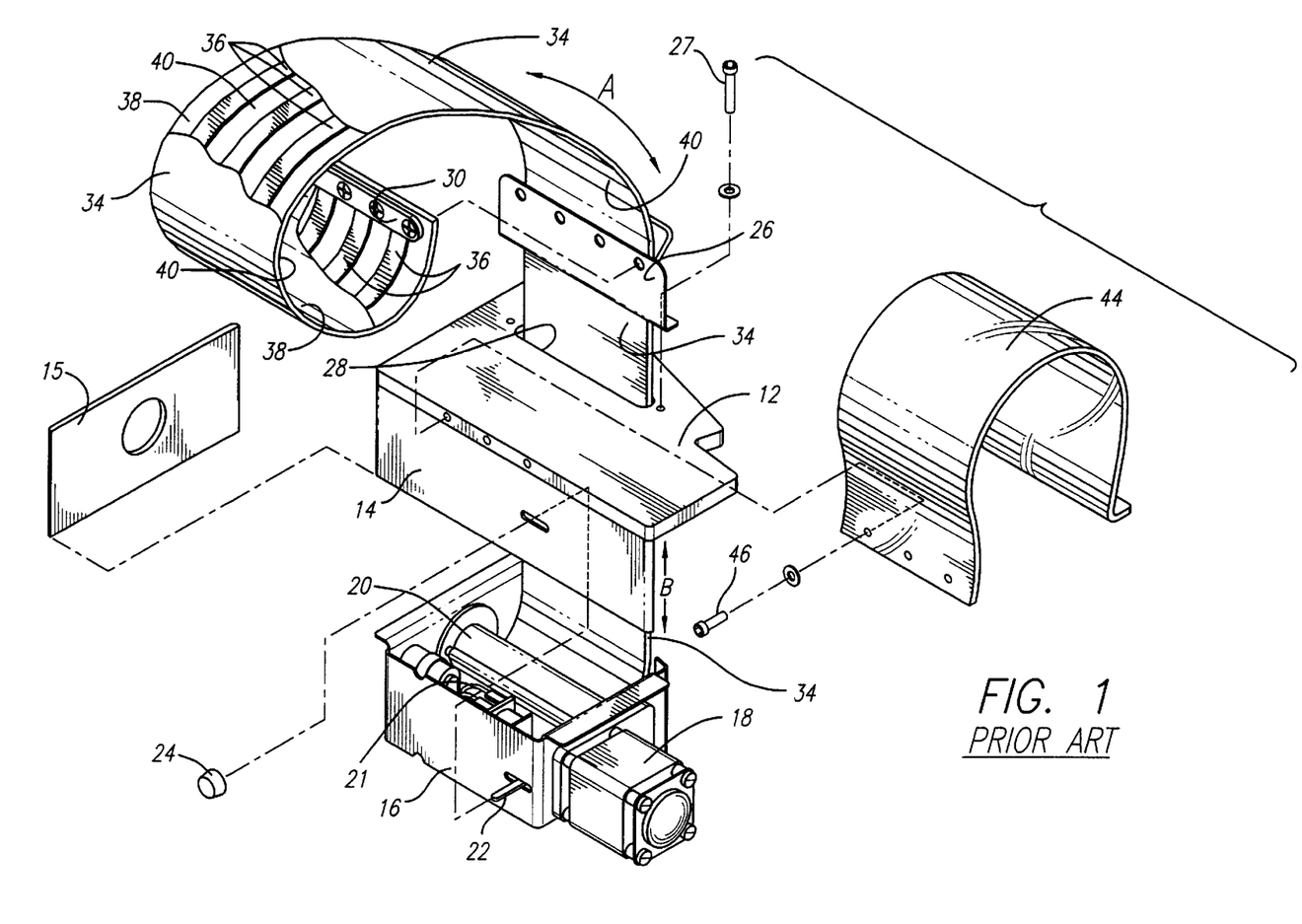
FIG. 1 is a partially exploded perspective view of a blood pressure cuff constructed according to the prior art.
Figure 2A:
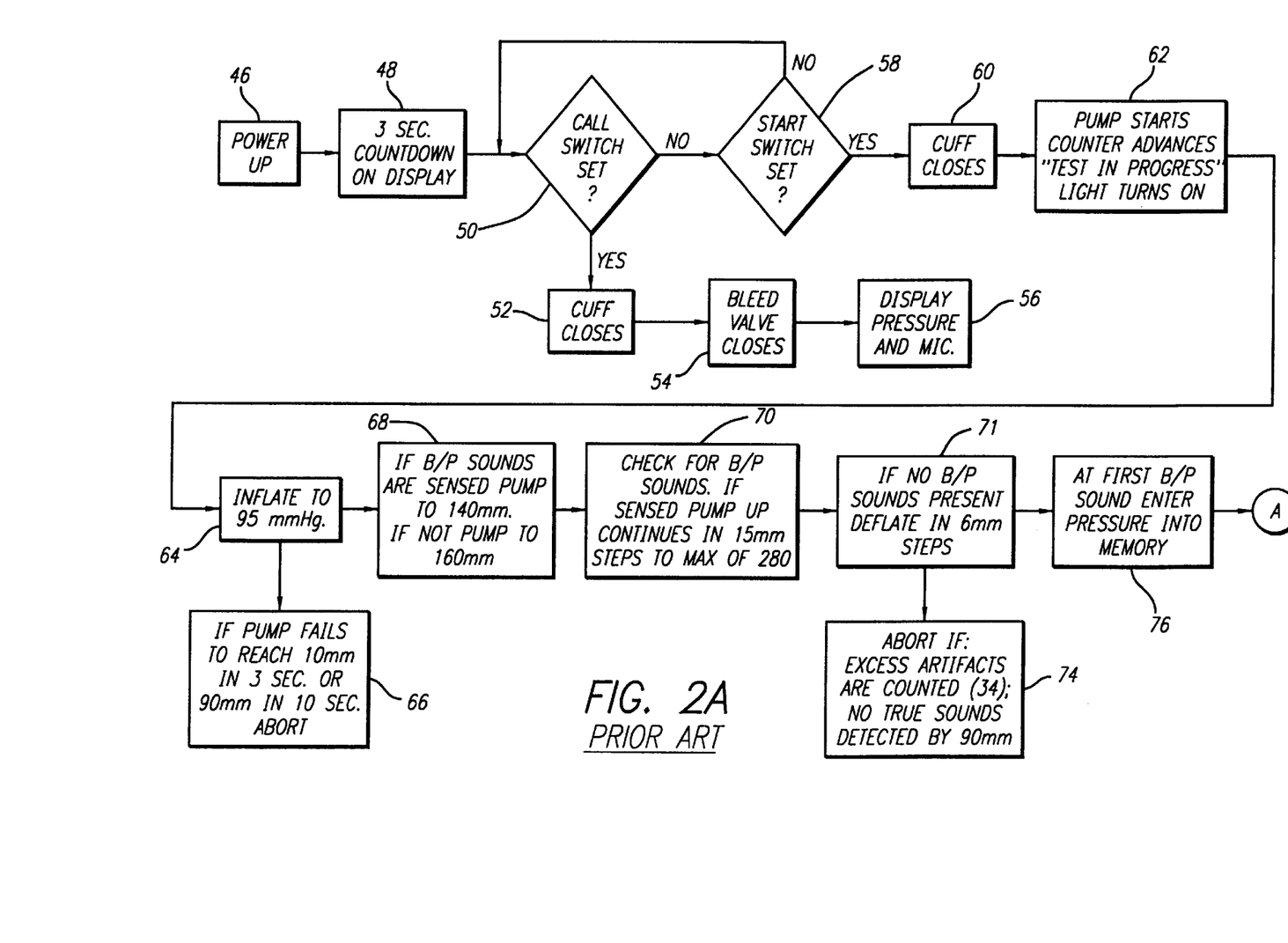
FIGS. 2A and 2B comprise a flow diagram of the operating
Figure 2B:
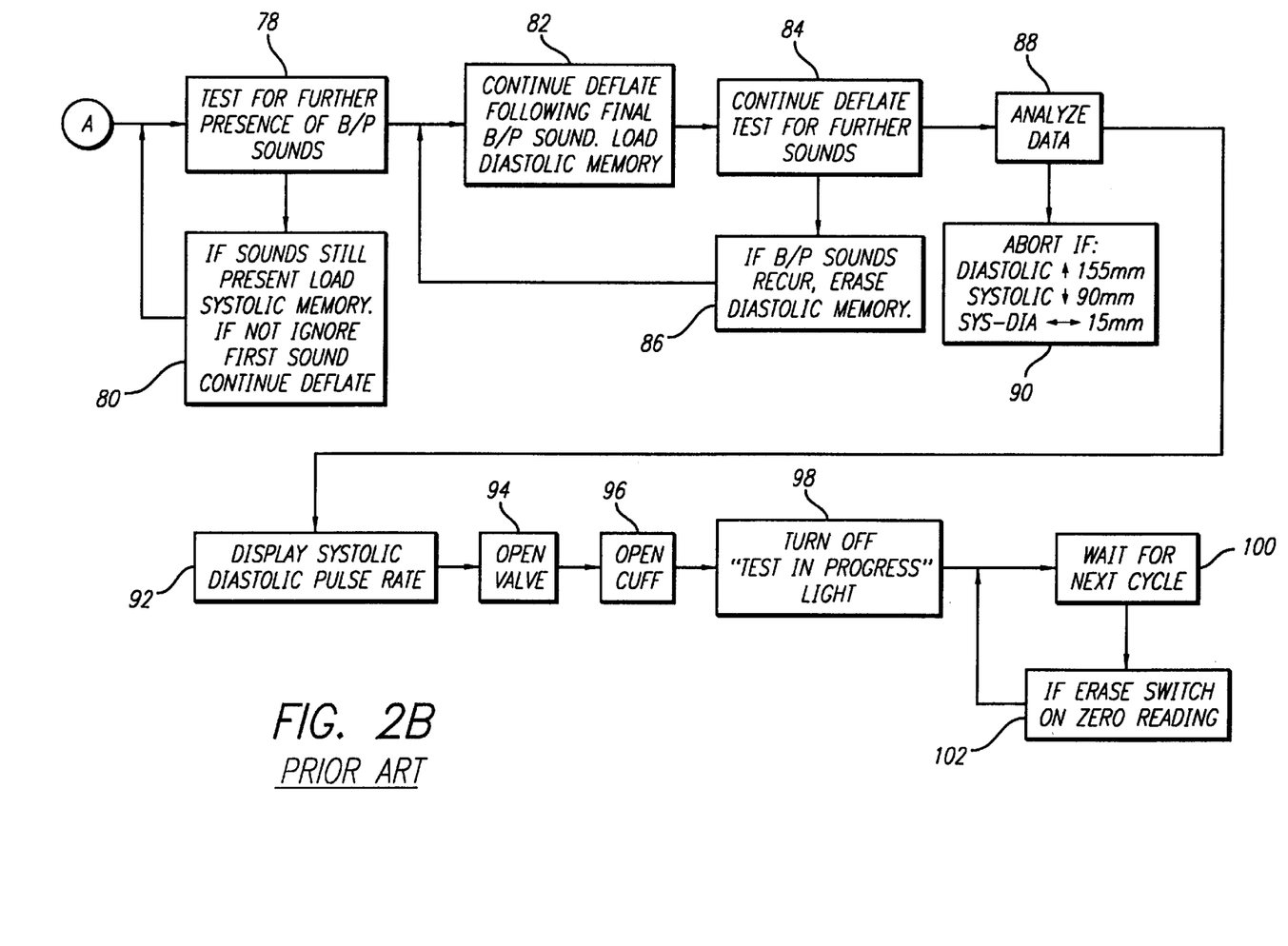

Reference first should be made to the prior art cuff shown in FIG. 1, the operation of which is described in the flow chart of FIGS. 2A and 2B. The device of FIG. 1 is a cuff which is in widespread use with automatic blood pressure machines. These machines are designed to enable persons to undertake a self evaluation blood pressure test in a short period of time. Typically, the machines are built into a frame which includes a surface for allowing the user to be seated in a proper position relative to the machine. These machines are ausculatory blood pressure machines, which use a microphone (electronic stethoscope) located in conjunction with an inflatable bladder for transmitting pulsating sounds representative of blood pressure to electronic circuitry located in the machine. The circuitry then includes counters and time interval measuring devices for detecting the muffling and disappearance of sound and for correlating the pulses supplied by the microphone to a display panel for displaying the systolic and diastolic blood pressure results to the user.

In order to obtain the necessary data for the systolic and diastolic blood pressure readings, a cuff assembly is provided. In the prior art, this cuff assembly was mounted on the top of the machine in a location to allow the user to conveniently insert his or her arm to a position where the cuff encircled the upper arm. As shown in FIG. 1, this portion of the machine included a base member having an upper surface 12 and a depending frame portion 14. The upper surface 12 includes a generally hollow cylindrical plastic housing 44, which is attached to the surface 12 by means of fasteners 46 in the position shown in FIG. 1. Inside the generally cylindrically shaped housing 44, a plate 26 is bolted adjacent a slot 28 in the top 12. This plate 26 has an attachment bar 30 for securing curved elongated spring fingers (three of which are shown) 36 to the support 26, as indicated in FIG. 1. These spring fingers 36 normally are biased outwardly to press toward the inside surface of the cylindrical housing 44. The outer surface of the fingers (the one adjacent the interior of the cylinder 44) is covered with an elongated rectangular flexible strip 34 made of cloth or other suitable material, which extends around the fingers 36 and downwardly through the slot 28, where it is attached to a take-up reel 20 located beneath the surface 12 in alignment with the slot 28.

The inside surface of the spring fingers 36 are covered by a blood pressure bladder 38 held in place by another cloth strip 40, which extends from the connecting plate 30 around the interior of the spring assembly shown in FIG. 1, to overlie the bladder 38. This strip 40 is secured to the strip 34. In the relaxed position, the strips 34 and 40 essentially are unwound from the take-up reel 20; and the spring fingers 36 press the entire assembly, including the uninflated bladder 38, into engagement with or nearly into engagement with the interior surface of the housing 44.

The take-up reel 20 is attached to a drive shaft on an electric motor 18, which is mounted on a mounting plate 16 is secured to the front plate 14 of the base of the device. Operating electronics 21 and a power supply for the motor 18 also are conveniently located adjacent the take-up reel 20. The front of the device includes an emergency release switch 22 with a control knob 24 attached to it, as shown in FIG. 1. As illustrated in FIG. 1, the flexible cloth band 34/40 moves in the direction of the arrow A shown at the top of the drawing in FIG. 1, and vertically, as shown by the double arrow B located beneath the upper surface 12 of the housing. An end plate 15 is secured on the left-hand end of the motor assembly to hold it in place under the top 12 of the housing and at the left-hand end of the motor assembly 18, 16, 20 which is shown in FIG. 1.

The operating sequence of the prior art device shown in FIG. 1 is illustrated in FIGS. 2A and 2B. A person desiring to use the device inserts his or her upper arm through the open cylindrical housing 44 into the space surrounded by the cuff assembly 34, 36, 38, 40 described above. At this time, the cuff assembly is in its relaxed or open position. A control (not shown) then initiates the power up 46 sequence shown in FIG. 2A. This initiates a three-second countdown on the display at 48, as shown. Once this countdown has been effected, a decision is made at 50 as to whether a call switch has been set. If the switch, indicating that a test to be run, has been set, the motor 18 is operated to rotate the shaft 20 to pull the flexible band 34 downwardly through the slot 28, as indicated by the arrows A and B in FIG. 1. In FIG. 2A this is indicated as "cuff closes" at 52. Once the cuff has been pulled to a position determined by the arm size, the motor 18 is turned off and a bleed valve 54 closes to permit a display of the pressure and the microphone output at 56.

If the call switch 50 was not set, a determination is made at 58 to check the status of a start switch. If the start switch has been set at 58, the cuff closes at 60; and the pump for supplying air to the cuff starts at 62 to advance a counter and to show a test in progress light (not shown) to turn on. The device then inflates to a pressure of 95 millimeters of mercury (mmHg) as shown If for any reason the pump fails to reach 10 millimeters of mercury (mmHg) in a three-second interval, or 90 millimeters in a ten-second interval, the system aborts and resets, as shown at 66. If, however, with normal operation of the system, the blood pressure sounds are sensed from a microphone (not shown) carried by the bladder spring assembly, the pump continues to increase the pressure in the bladder in 15 mmHg steps to a maximum of 280 mmHg at 70. When blood flow has been constricted and no blood pressure sounds are present, the system deflates in 6 mmHg steps at 72 until the first blood pressure sound is detected at 76. This sound then is entered into memory. However, if excess artifacts (extraneous sounds) are counted or if no true sounds are detected by 90 mmHg at 74, the system aborts and resets.

If blood pressure sounds are heard and are being entered into memory at 76, the system continues as shown in FIG. 2B. At detection of the first sounds at 76, tests continue for further evidence of blood pressure sounds at 78. If the sounds are still present, the systolic memory is loaded at 80. If the sounds are not present, they are ignored; and the system continues to deflate in 6 millimeter steps as previously described at 72. This test at 78, or the loading of the systolic memory at 80, continues with step-by-step deflation in 6 mmHg steps until the final blood pressure sound. At this time, the diastolic memory is loaded at 82. The test then continues deflation at 84 for further sounds; and the data is analyzed at 88. If, however, at 84 the blood pressure sounds recur, the diastolic memory is erased at 86; and the system continues to operate with deflation at 82 until the final blood pressure sound is detected, at which time the diastolic memory is loaded.

At the data analysis at 88, the system aborts if the diastolic blood pressure which is recorded in the memory is equal to or greater than 155 mmHg, or the systolic blood pressure is equal to or less than 90 mmHg, or the difference between the systolic and diastolic pressure is 15 mmHg or less, as indicated at 90. If these conditions do not occur, however, the systolic and diastolic pulse rates are displayed on the machine display (not shown) at 92. At this time, the bleed valve is opened at 94 to exhaust air from the bladder 38; and the cuff is opened at 96. For the machine shown in FIG. 1, this includes the reverse operation of the motor 18 to unwind the strips 34/40 and allow the springs 36 to pull the cuff up and away from the arm into the standby position adjacent the inner wall of the housing 44. When the cuff is opened at 96, a test in progress light (not shown) is turned off at 98; and the system is restored to waiting for the next cycle at 100. If the erase switch is on, the reading also is zeroed at 102, and the system is prepared for its next cycle of operation.

Figure 3:
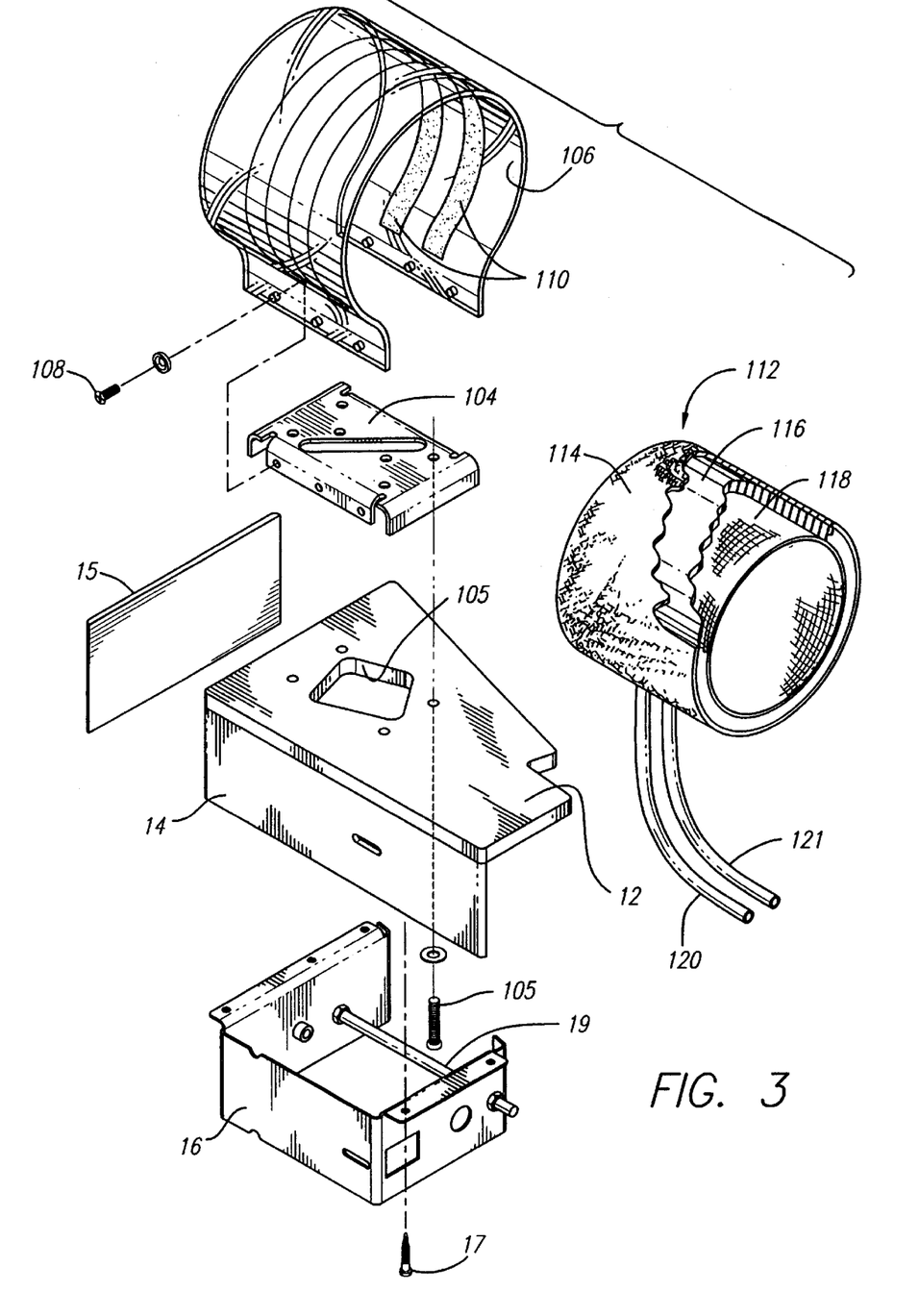
FIG. 3 is an exploded perspective view of a preferred embodiment of the invention.

In contrast to the system which has been described in conjunction with the prior art test assembly of FIG. 1 and the operation of the system as described in FIGS. 2A and 2B, a cuff in accordance with the preferred embodiment of the invention is shown in FIG. 3. The cuff assembly of FIG. 3 is mounted on a base including a top 12 and a downwardly depending front panel 14, which is quite similar to the correspondingly numbered components shown in FIG. 1. The housing 16 is not used for a motor assembly. This housing instead may be employed to route air delivery lines and air removal lines and control valves coupled to air delivery and air removal lines 120 and 121, respectively, shown in FIG. 3. A support rod 19 is used to hold the control valves for accomplishing this; but the particular configuration of the housing 16 is not important. The motor 18 and the take-up reel 20 are removed from the housing 16, since they no longer are used with the embodiment shown in FIG. 3.

The embodiment shown in FIG. 3 also includes a generally open ended cylindrical housing 106, which is comparable in its dimensions to the housing 44 shown in FIG. 1. The housing 106, however, is attached on opposite edges, along its open bottom, to a mounting plate 104 by means of suitable fasteners 108. The plate 104 then is secured, by means of four fasteners 105 (only one of which is shown in FIG. 3), over an opening 105 in the top 12 of the base.

The interior surface of the cylindrical housing 106 has mounting strips 110 made of one portion of a hook-and-loop fastener secured to it. These strips 110 extend along the greater part of the interior surface of the cylindrical housing 106, essentially encircling the opening which exists through the housing 106.

A cuff 112, which has a generally cylindrical configuration corresponding to the internal dimensions of the housing 106, is inserted into the housing 106 over the plate 104. The cuff includes three layers. The outer layer 114 is made either partially or entirely of material comprising the other half of a hook-and-loop fastener; so that it is securely (but releasably) engaged by the strips 110 to hold the cuff in place in the housing 106. An inner layer 118 of the cuff is secured around its edges to the layer 114 to form an enclosed space into which an inflatable bladder 116. The bladder 116 substantially encircles the area which is enclosed by the cuff 112, and is connected at its bottom through an air delivery tube 120 and an air removal tube 121. The tubes 120 and 121 extend through the slot in the assembly member 104 and through the hole 105 in the top 12 of the base into the housing 16.

It is important to note that in the embodiment shown in FIG. 3 there are no moving mechanical parts. The only part which moves in any way is the bladder 116, its movement being effected by means of inflation and deflation which expands and contracts its size to cause the inner material 118 of the cuff to press against the arm of a person using the device when it is inflated. When it is deflated, the cuff retracts to a standby position, wherein all three of the layers 114, 116 and 118 essentially conform to or lie adjacent the interior surface of the housing 106. The bladder 116, which is used with the embodiment shown in FIG. 3 is designed to have a greater capacity for expansion and contraction than the bladder 38 used in conjunction with the prior art mechanical device shown in FIG. 1, since the entire closure of the cuff on the arm of a person using the device of FIG. 3 is effected by means of air pressure without any additional mechanical movement of the various parts.

Figure 4A:
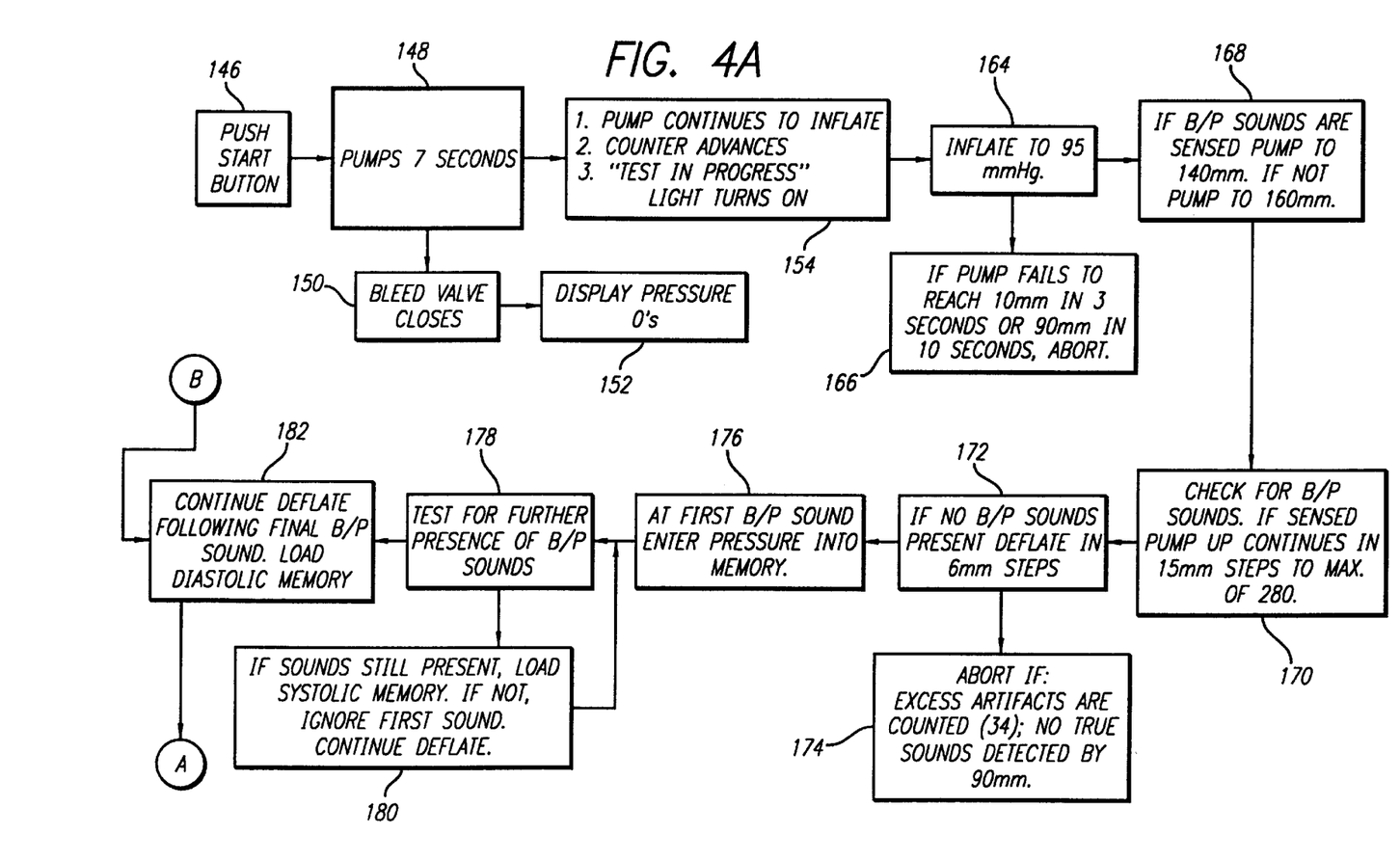
FIGS. 4A and 4B are a flow diagram of the operating sequence of the device shown in FIG. 3.
Figure 4B:
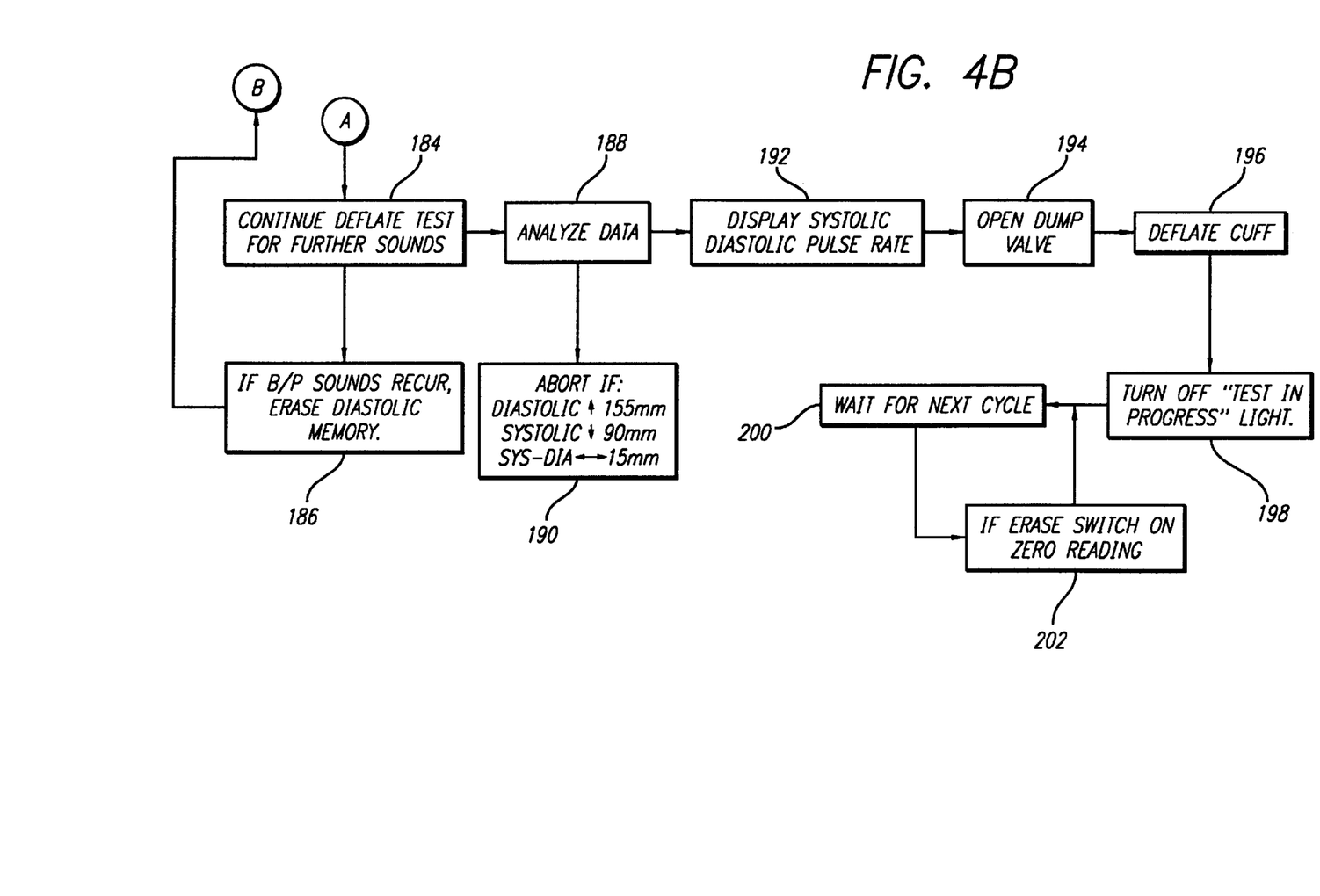

FIGS. 4A and 4B constitute a flow diagram describing the operation of the cuff of the embodiment of the invention shown in FIG. 3. Initially, a push start button 146 is operated by the user after his or her arm has been inserted to cause the upper arm to be encircled by the interior material 118 of the cuff located inside the housing 110. This causes a conventional air pump (not shown) to pump for seven seconds at 148. The bleed valve is closed at 150 and the pressure is displayed at 152, on a display (not shown) on the device at 152. As shown at 154, the pump continues to inflate; and the counter advances with a test in progress light (not shown) turned on. The device continues to inflate to 95 mmHg at 164, similar to the inflation shown at 64 in FIG. 2A of the prior art device. As with the prior art device, if blood pressure sounds are sensed at 168, the pump continues to pump to 140 mmHg. If the sounds are not sensed, the pump continues to pump to 160 mmHg at 168. In fact, the operation of the device shown in FIG. 3 is identical to the operation of the device shown in FIG. 1 from steps 64 through 94 (which are similarly numbered as steps 164 through 194 in FIGS. 4A and 4B). For this reason, these steps of the operating sequence of a blood pressure test are not described here; and reference can be made to the previous description of steps 64 through 94 of FIGS. 2A and 2B for a correlation.

At step 194, however, the dump valve 194 is opened; and the air is removed from the bladder 116 through the air removal tube 121 shown in FIG. 3. Typically, this air is dumped into the surrounding ambient air. When this occurs, the cuff is deflated at 196, and the test in progress light is turned off at 198. The system then is prepared for the next cycle at 200. Once again, if the erase switch is on, the reading display is zeroed at 202, and, again the system is prepared for waiting for the next cycle at 200.

It should be noted that the difference between the system shown and described in FIGS. 3 and 4A and 4B operates identically to the prior art device during the time the blood pressure test itself is being taken. The sequencing of pumps and valves in order to provide the pressure signals picked up by the microphone to provide the systolic and diastolic readings is the same. Consequently, the same electronics and control circuitry is employed for both devices of FIG. 1 and FIG. 3. The device of FIG. 3, however, requires significantly less maintenance in its operation. The device of FIG. 3 also overcomes the potential for obese or elderly people with loose skin being pinched between the moving parts, since this possibility does not exist with the device of FIG. 3.

The foregoing description of the preferred embodiment of the invention is to be considered illustrative and not as limiting. Various changes and modifications will occur to those skilled in the art for performing substantially the same function, in substantially the same way, to achieve substantially the same result, without departing from the true scope of the invention as defined in the appended claims.

What is claimed is:

1. An improved blood pressure cuff including in combination:

a base support member;

a generally cylindrically shaped housing mounted on the base support member and having an internal diameter larger than the external diameter of an arm to be inserted therethrough, the cylindrical housing being open at both ends;

a hollow sleeve having a first portion generally overlying and attached to the interior of the cylindrical housing and having a mating second portion overlying the first portion and attached thereto to form a space between the first and second portions;

an inflatable bladder located in the space between the first and second portions of said hollow sleeve;

an air supply device for supplying air under pressure to the bladder to inflate the bladder, thereby expanding the second portion of the hollow sleeve into the interior space in the cylindrical housing; and a device for removing air from the bladder.

2. The combination according to claim 1 wherein the first portion of the hollow sleeve is releasably attached to the interior of the cylindrical housing.

3. The combination according to claim 2 wherein the bladder and the second portion of the sleeve return to a first position when substantially all of the air is removed from the bladder, with the first position substantially causing the hollow sleeve and the bladder to generally conform to the interior of the cylindrical housing.

4. The combination according to claim 3 wherein the bladder has a length which is slightly less than the internal circumference of the housing.

5. The combination according to claim 4 wherein the generally cylindrical housing has an open slot therein for effecting mounting of the housing on the base support member.

6. The combination according to claim 5 wherein the device for supplying air and the device for removing air extend through the open slot in the cylindrical housing and through the first portion of the hollow fabric sleeve for supplying air to and removing air from the bladder.

7. The combination according to claim 6 wherein the first and second portions of the sleeve are elongated rectangular members of substantially the same dimensions, with first and second ends, and wherein the second portion is placed over the first portion to overlie the same, with mating edges of the first and second portions being secured to one another leaving a space between the first and second portions, and wherein the first and second ends are joined together to form the hollow sleeve.

8. The combination according to claim 7 wherein the bladder has an overall length which is less than the length of the rectangular members of the sleeve, and wherein the bladder has first and second ends, each located on opposite sides of said slot in said cylindrical housing.

9. The combination according to claim 8 further including hook-and-loop fastening means for effecting releasable attachment of the first portion of the hollow sleeve to the interior of the cylindrical housing.

10. The combination according to claim 9 wherein the first and second portions of said sleeve are made of fabric.

11. The combination according to claim 1 wherein the generally cylindrical housing has an open slot therein for effecting mounting of the housing on the base support member.

12. The combination according to claim 11 wherein the device for supplying air and the device for removing air extend through the open slot in the cylindrical housing and through the first portion of the hollow fabric sleeve for supplying air to and removing air from the bladder.

13. The combination according to claim 1 wherein the first and second portions of said sleeve are made of fabric.

14. The combination according to claim 13 further including hook-and-loop fastening means for effecting releasable attachment of the first portion of the hollow sleeve to the interior of the cylindrical housing.

15. The combination according to claim 14 wherein the bladder and the second portion of the sleeve return to a first position when substantially all of the air is removed from the bladder, with the first position substantially causing the hollow sleeve and the bladder to generally conform to the interior of the cylindrical housing.

16. The combination according to claim 1 wherein the first and second portions of the sleeve are elongated rectangular members of substantially the same dimensions, with first and second ends, and wherein the second portion is placed over the first portion to overlie the same, with mating edges of the first and second portions being secured to one another leaving a space between the first and second portions, and wherein the first and second ends are joined together to form the hollow sleeve.

17. The combination according to claim 16 wherein the bladder has an overall length which is less than the length of the rectangular members of the sleeve, and wherein the bladder has first and second ends, each located on opposite sides of said slot in said cylindrical housing.

18. The combination according to claim 17 wherein the bladder has a length which is slightly less than the internal circumference of the housing.

19. The combination according to claim 2 further including hook-and-loop fastening means for effecting releasable attachment of the first portion of the hollow sleeve to the interior of the cylindrical housing.

20. The combination according to claim 1 wherein the bladder and the second portion of the sleeve return to a first position when substantially all of the air is removed from the bladder, with the first position substantially causing the hollow sleeve and the bladder to generally conform to the interior of the cylindrical housing.

* * * * *